(12) United States Patent
Rezai et al.

(10) Patent No.: US 7,769,470 B1
(45) Date of Patent: *Aug. 3, 2010

(54) NEUROMODULATION DEVICE AND METHOD OF USING SAME

(75) Inventors: Ali Rezai, Shaker Heights, OH (US); John Hall, Grand Rapids, MI (US); Barry D. Kuban, Avon Lake, OH (US); Ken Baker, Chesterland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 670 days.

This patent is subject to a terminal disclaimer.

(21) Appl. No.: 11/641,860

(22) Filed: Dec. 20, 2006

Related U.S. Application Data

(63) Continuation of application No. 10/603,243, filed on Jun. 24, 2003, now Pat. No. 7,181,288.

(60) Provisional application No. 60/391,260, filed on Jun. 24, 2002, provisional application No. 60/391,261, filed on Jun. 24, 2002.

(51) Int. Cl.
*A61N 1/04* (2006.01)

(52) U.S. Cl. .......................... 607/116; 607/45; 607/117

(58) Field of Classification Search .................. 607/45, 607/116, 117, 122, 123, 126, 128, 98; 600/585; 604/22, 248
See application file for complete search history.

(56) References Cited

U.S. PATENT DOCUMENTS

| | | | |
|---|---|---|---|
| 5,454,782 A * | 10/1995 | Perkins | ........................ 604/20 |
| 5,868,740 A | 2/1999 | LeVeen et al. | |
| 6,050,992 A | 4/2000 | Nichols | |
| 6,129,685 A | 10/2000 | Howard, III | |
| 6,185,464 B1 | 2/2001 | Bonner et al. | |
| 6,319,241 B1 | 11/2001 | King et al. | |
| 6,343,226 B1 | 1/2002 | Sunde et al. | |
| 6,353,762 B1 | 3/2002 | Baudino et al. | |
| 6,969,388 B2 * | 11/2005 | Goldman et al. | .............. 606/41 |
| 2002/0062143 A1 * | 5/2002 | Baudino et al. | ............. 607/116 |
| 2002/0183740 A1 | 12/2002 | Edwards et al. | |
| 2003/0036755 A1 * | 2/2003 | Ginn | ........................... 606/41 |
| 2003/0229386 A1 * | 12/2003 | Rosenman et al. | .......... 607/116 |

* cited by examiner

*Primary Examiner*—Carl H Layno
*Assistant Examiner*—Jennifer Stewart
(74) *Attorney, Agent, or Firm*—Kenyon & Kenyon, LLP

(57) ABSTRACT

A device for modulating a volume of neural tissue comprising: a cannula having a proximal end, a distal end, and a lumen extending to at least the distal end, an actuator mechanism at least partially disposed in the lumen of the cannula; a plurality of leads having at least one electrode disposed thereon, the plurality of leads being coupled to the actuator mechanism to reciprocate between a retracted position wherein the plurality of leads are radially constrained within the lumen and an extended position; and a guide provided at the distal end of the cannula to deflect the plurality of leads radially outwardly into the neural tissue when the actuator mechanism is moved to the extended position.

15 Claims, 8 Drawing Sheets

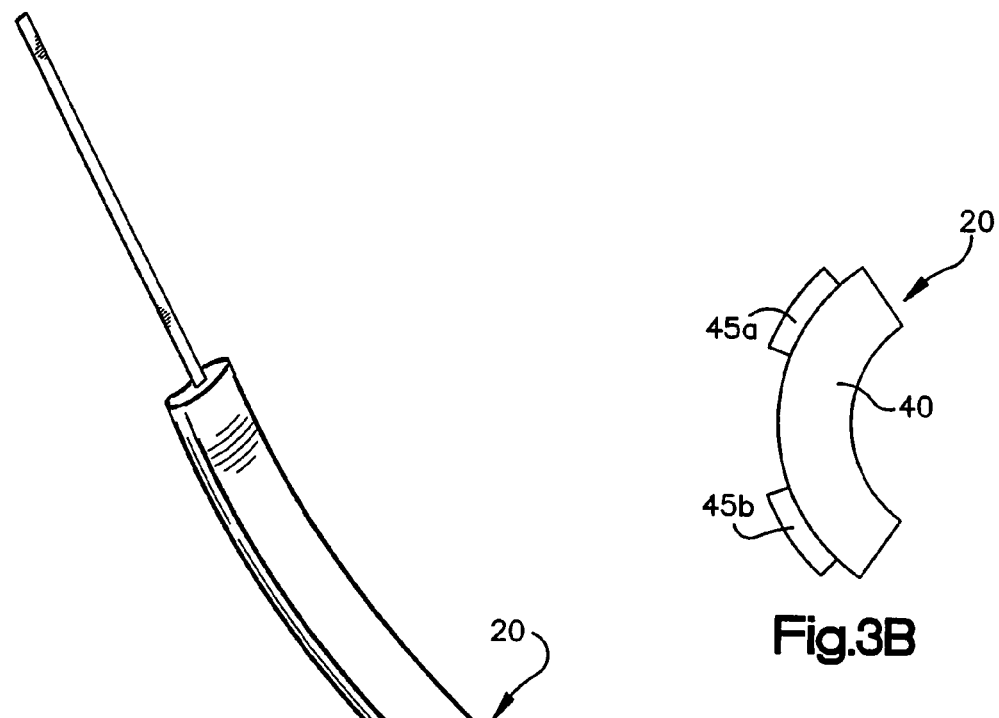
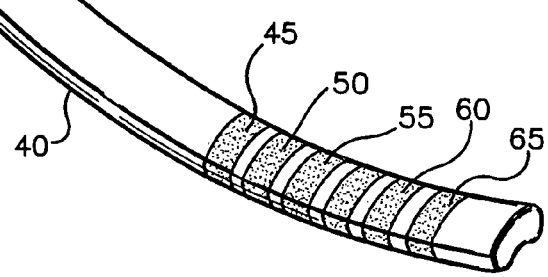
Fig.3A
Fig.3B
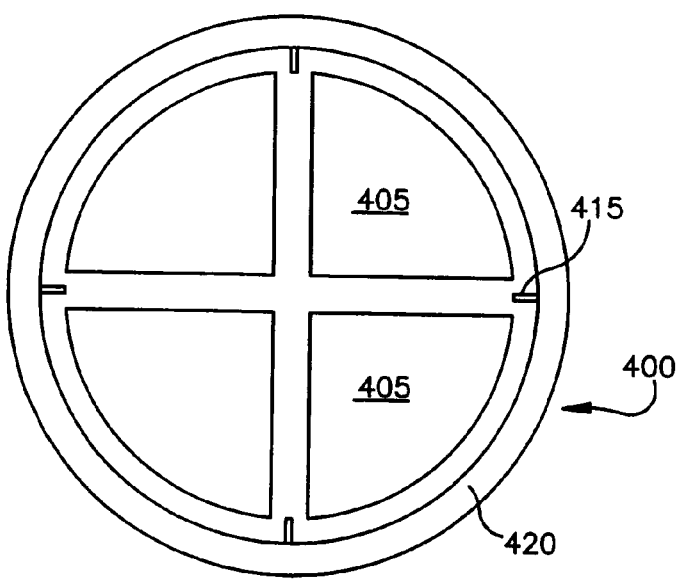
Fig.4

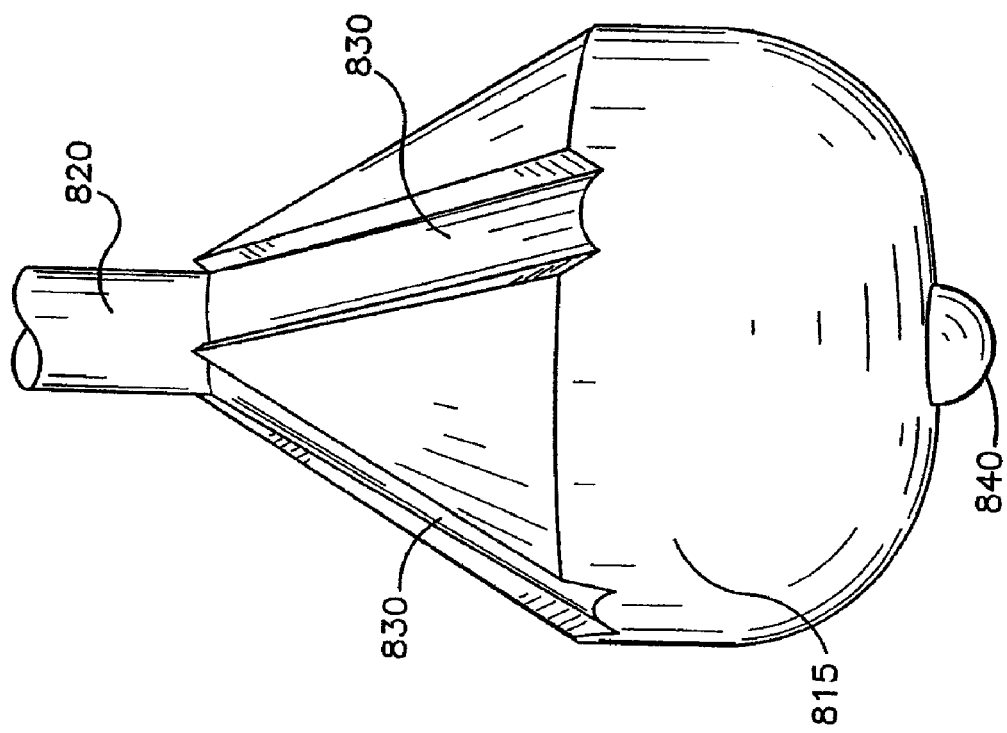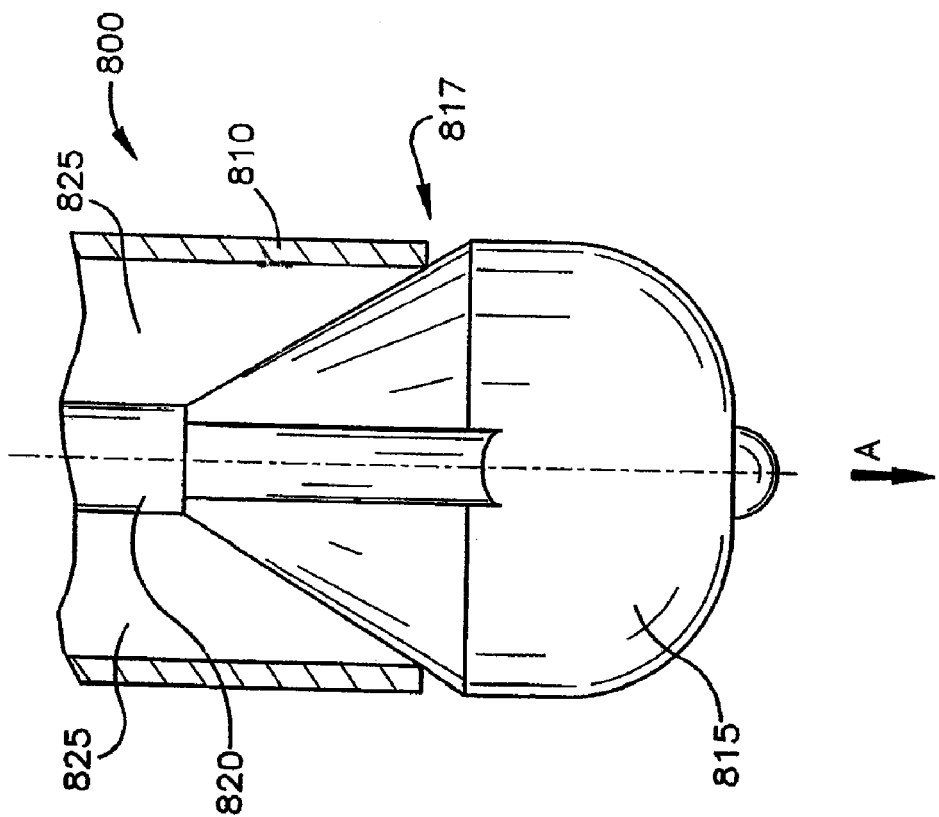

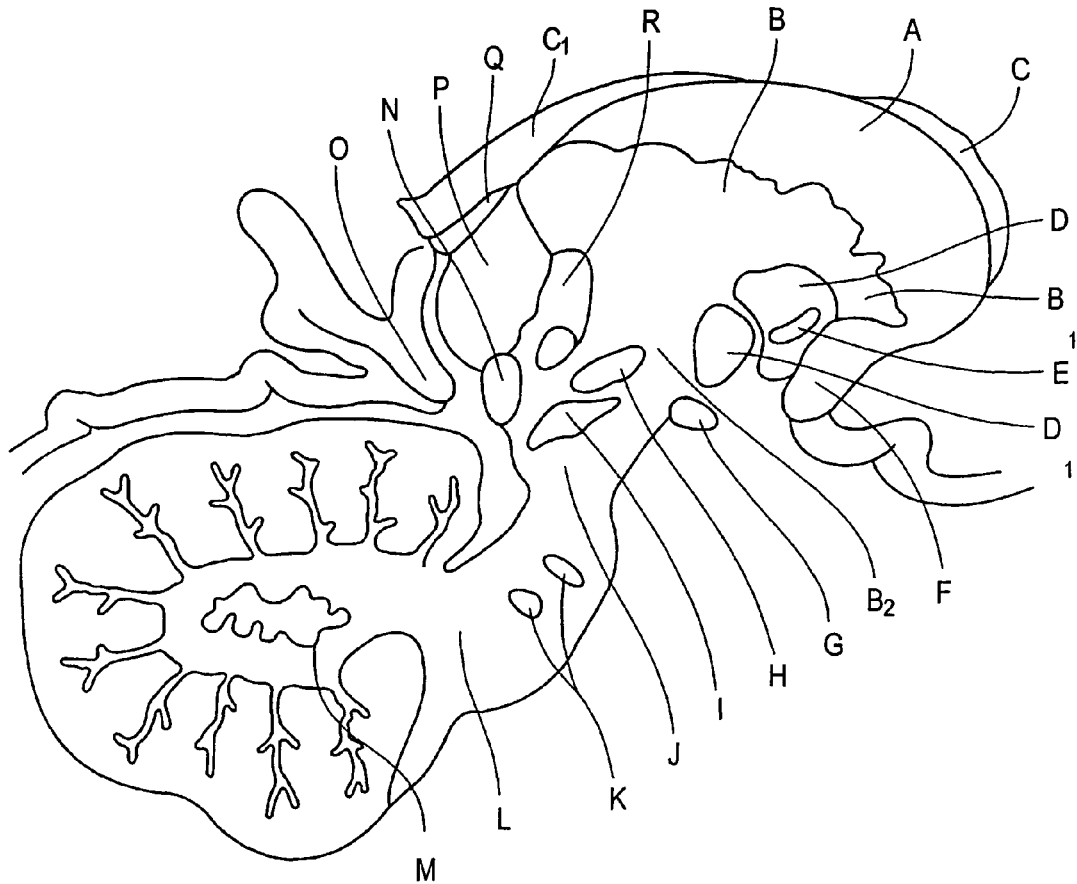

| | | |
|---|---|---|
| A CAUDATE NUCLEUS | D GLOBUS PALLIDUS (EXTERNAL SEGMENT) | K PONTINE NUCLEI |
| B GENU OF INTERNAL CAPSULE | D₁ GLOBUS PALLIDUS (INTERNAL SEGMENT) | L MIDDLE CEREBELLAR PEDUNCLE |
| B₁ ANTERIOR LIMB OF INTERNAL CAPSULE | E ANTERIOR COMMISSURE | M DENTATE NUCLEUS |
| B₂ POSTERIOR LIMB OF INTERNAL CAPSULE | F PUTAMEN | N MEDIAL GENICULATE NUCLEUS |
| C ANTERIOR HORN OF LATERAL VENTRICLE | G OPTIC TRACT | O CINGULATE CYRUS |
| | H SUBTHALAMIC NUCLEUS | P PULVIGAR |
| C₁ BODY OF LATERAL VENTRICLE | I SUBSTANTIA NIGRA | Q CRUS OF FORNIX |
| | J BASIS PEDANCULA | R VENTRAL POSTERIOR LATERAL NUCLEUS |

Fig.9

NEUROMODULATION DEVICE AND METHOD OF USING SAME

CROSS-REFERENCE TO RELATED APPLICATIONS

This application is a continuation application from application Ser. No. 10/603,243 filed Jun. 24, 2003 which claims priority to U.S. Provisional Application Nos. 60/391,260 and 60/391,261 both filed Jun. 24, 2002, which are both incorporated by reference in their entireties.

BACKGROUND OF THE INVENTION

In the case of deep brain stimulation (DBS), it is particularly critical that the stimulation lead be properly positioned. If the lead is not properly positioned and needs to be moved, it must be removed and re-inserted thereby increasing the risk of bleeding and damage to the neural tissue. It is therefore desirable to place the lead within the brain in one attempt and avoid subsequent movement or repositioning of the lead.

These steering techniques, however, are limited to primarily two-dimensional steering since the electrodes are positioned in a linear or planar configuration. In the case of deep brain stimulation (DBS), the stimulation treatment requires stimulation of a volume of neural tissue. Since the exact location of the desired tissue is unknown, it is desirable to steer the electrical field in more than just two-dimensional space.

BRIEF DESCRIPTION OF THE DRAWINGS

It will be appreciated that the illustrated boundaries of elements (e.g., boxes or groups of boxes) in the figures represent one example of the boundaries. One of ordinary skill in the art will appreciate that one element may be designed as multiple elements or that multiple elements may be designed as one element. An element shown as an internal component of another element may be implemented as an external component and vice versa.

Further, in the accompanying drawings and description that follow, like parts are indicated throughout the drawings and description with the same reference numerals, respectively. The figures are not drawn to scale and the proportions of certain parts have been exaggerated for convenience of illustration.

FIG. 3A illustrates a perspective view of a lead 20 that can be used in the device 10;

FIG. 3B illustrates a cross-section view of one embodiment of the lead 20;

FIG. 4 illustrates a bottom view of one embodiment of a cannula 400 configured to prevent relative movement of a plurality of leads 405 contained therein;

FIGS. 8A-8D illustrates multiple views of another embodiment of a neuromodulation device 800 configured to deploy multiple leads out of a single opening in a three-dimensional volume of tissue;

FIG. 9 illustrates a schematic of the human brain sectioned through the dentate nucleus.

DETAILED DESCRIPTION OF THE INVENTION

Figure 1:
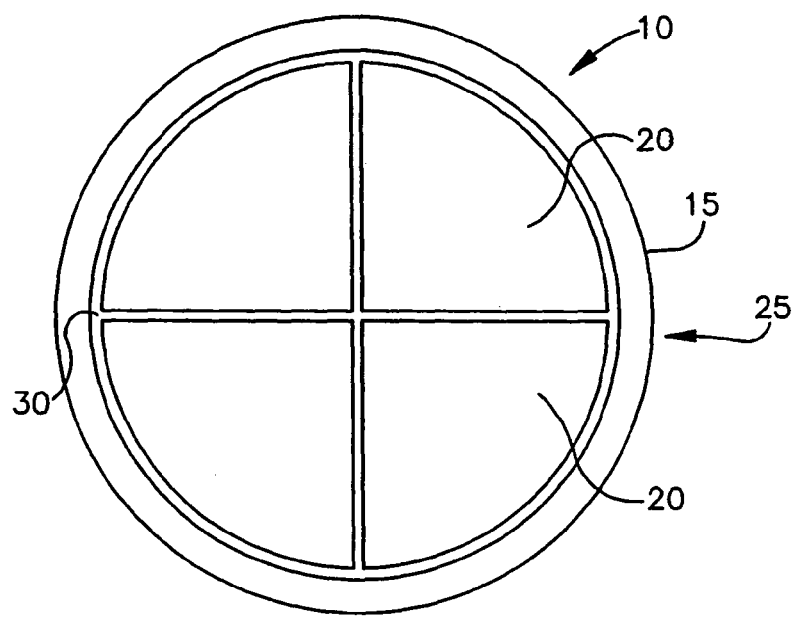
FIG. 1 illustrates a bottom view of one embodiment of a neurostimulation device 10.

FIG. 1 illustrates a bottom view of one embodiment of a neurostimulation device 10. The neurostimulation device 10 includes a cannula 15 and a plurality of individual leads 20 constrained within a lumen of the cannula 15. The plurality of leads 20 can be movable between a retracted position (as shown in FIG. 1) and an extended position.

The cannula 15 has a proximal end (not shown) for accepting the plurality of leads 20 and a distal end 25 having an opening 30 configured to permit the leads 20 to be advanced out of the opening 30 in the cannula 15. The cannula 15 may be formed from any metal, plastic, or the like, and may be electrically active or inactive depending on the manner in which electrical energy is to be applied.

In one embodiment, each lead 20 has a "pie shaped" cross-section such that all of the leads 20 can form a circular cross-section when the leads 20 are constrained in the cannula 15. For example, each individual lead can be placed adjacent to the other lead 20 such that the flat side of one given lead is in contact with, or closely positioned adjacent to, the flat side of another adjacent lead. Once positioned in the cannula 15, each lead 20 can be prohibited from rotating by the existence of its adjacent leads. It will be appreciated that any number of "pie" shaped leads can be used in the device 10. Additionally, it will be appreciated that two leads 20 can be used in the device 10 having a semi-circular cross-section.

Figure 2:
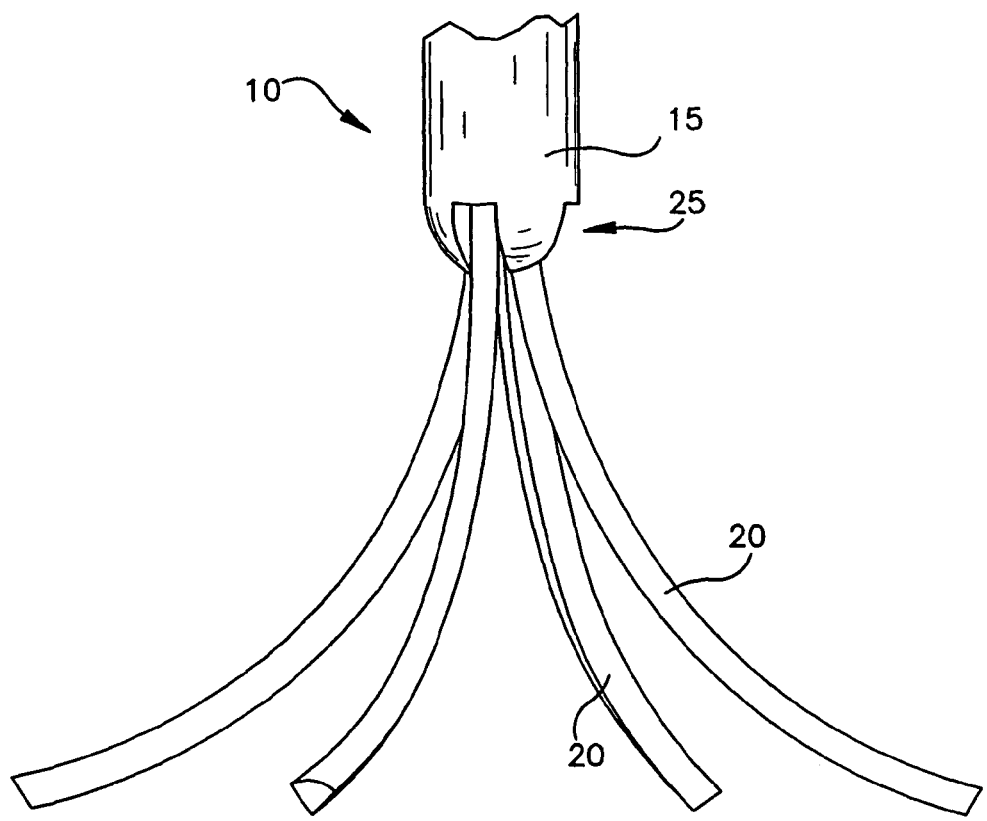
FIG. 2 illustrates a perspective view of the neurostimulation device 10 in the extended position.

FIG. 2 illustrates a perspective view of the neurostimulation device 10 in the extended position. In one embodiment, the leads 20 can be deployed in an array emanating generally from a target site within the treatment region of the tissue. For example, the array can be a three-dimensional array to reach a volume of tissue. To permit the leads to extend into a three-dimensional array, the leads 20 can be configured to be pre-bent into an arcuate shape and have a memory to retain such arcuate shape. For example, as the leads 20 are being deployed into the extended position, the leads 20 can exit the cannula 15 along an arcuate path that can be controlled by the pre-bent arcuate shape of the leads 20. Such leads 20 can be formed from conductive metals having a suitable shape memory, such as stainless steel, nickel-titanium alloys, nickel-chromium alloys, spring steel alloys, and the like.

FIG. 3A illustrates a perspective view of a lead 20 that can be used in the device 10. Each lead 20 includes a support form or substrate 40 having a plurality of electrodes bands 45, 50, 55, 60, 65. Although five electrode bands are illustrated in FIG. 3A, it will be appreciated that any number of electrode bands may be disposed on each lead.

In one embodiment, the electrode bands do not form a continuous electrode surface, but rather the bands are segmented into a plurality of individual electrodes. For example, as shown in FIG. 3B which is a cross-section view of a lead 20 similar to the lead 20 shown in FIG. 3A, electrodes 45a, 45b can be substantially electrically isolated from each other. Electrical connectivity to a signal generator (not shown) can be provided by conductors (not shown).

In other embodiments, a single electrode or multiple electrically connected electrodes can extend completely or partially around the perimeter of the lead 20. As can now be appreciated, individual electrodes forming a band can range in an angular distance around the exterior of the supporting surface 40 by as little as a few degrees to as much completely around the supporting surface.

It can now be appreciated that each individual electrode can be selectively powerable. This control provides a desired, focused (i.e. directed) electrical field around the lead 20. For example, electrodes may be powered to stimulate an area adjacent thereto while substantially minimizing the signal in an area adjacent to electrodes on the other side of the lead. Alternatively, opposing electrodes can be powered to produce a signal that destructively interferes with the desired signal. The shape of the field will vary with the power applied, the number and arrangement of electrodes, and particular shapes and sizes chosen for the electrodes.

In operation, the device 10 will be first introduced into the target site as the leads 20 are in the retracted position. Once the device 10 has been implanted, the leads 20 can be moved to the extended position such that the leads 20 are deployed in the desired three-dimensional array. In one embodiment, the leads 20 can diverge radially outwardly from the cannula 15 (located at the target site) into the target site in a uniform pattern, i.e. with the spacing between adjacent electrodes diverging in a substantially uniform and/or symmetric pattern. In the exemplary embodiments, pairs of adjacent leads will be spaced-apart from each other in similar or identical, repeated patterns and will usually be symmetrically positioned about an axis of the cannula 15. The leads 20 may extend or project along generally straight lines from the target site, but will more usually be shaped to curve radially outwardly and optionally to evert proximally so that they face partially or fully in the proximal direction when fully deployed. It will be appreciated that a wide variety of particular patterns can be provided to uniformly cover the region to be treated. Electrical current can then be applied through the electrodes in either a monopolar or bipolar fashion.

In other cases, the cannula 15 may be introduced using an internal stylet which is subsequently exchanged for the electrode array. In this case, the cannula can be relatively flexible since the initial column strength will be provided by the stylet. The cannula serves to constrain the individual leads in a radially collapsed configuration to facilitate their introduction to the tissue target site. The leads can then be deployed to their desired configuration, usually a three-dimensional configuration, by extending distal ends of the electrode elements from the distal end of the cannula into the tissue. In the preferred case of the tubular cannula, this can be accomplished simply by advancing the distal ends of the leads distally from the cannula so that they emerge and deflect (usually as a result of their own spring or shape memory) in a radially outward pattern.

Illustrated in FIG. 4 is a bottom view of one embodiment of a cannula 400 configured to prevent relative movement of a plurality of leads 405 contained therein. The cannula 400 includes a plurality of tabs 415 provided on an interior wall 420 of the cannula 400. The tabs 415 can be positioned in the cannula 400 such that an individual lead (not shown) can fit between adjacent tabs 415 thereby substantially preventing rotational movement of the leads 405. The tabs 415 can also assist in the separation of adjacent leads prior to entering the tissue.

Figure 5:
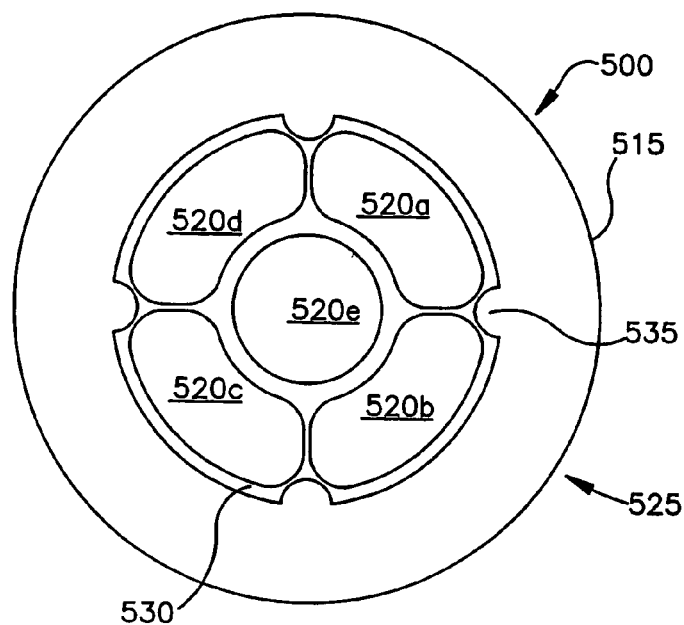
FIG. 5 illustrates a bottom view of another embodiment of a neurostimulation device 500.

Illustrated in FIG. 5 is a bottom view of another embodiment of a neurostimulation device 500. The neurostimulation device 500 includes a cannula 515 and a plurality of individual leads 520 constrained within a lumen of the cannula 515. The plurality of leads 520 can be movable between a retracted position (as shown in FIG. 5) and an extended position.

The cannula 515 has a proximal end (not shown) for accepting the plurality of leads 520 and a distal end 525 having an opening 530 configured to permit the leads 520 to be advanced out of the opening 530 in the cannula 515. In one embodiment, the cannula 515 may include tabs 535 to prevent rotational movement of the leads 520 within the cannula 515. The cannula 515 may be formed from any metal, plastic, or the like, and may be electrically active or inactive depending on the manner in which electrical energy is to be applied.

In one embodiment, the plurality of leads 520 can include four outer leads 520a-d and a central lead 520e. The outer leads 520a-d may have a cross section that takes the shape of a "curved" trapezoid, while the central lead 520e has a circular cross section. In this embodiment, the ends of leads 520 may be rounded (not shown) at the tip to assist in advancing the cannula 515 to the target site in the tissue. It will be appreciated that any number of outer leads can be positioned within the cannula 515. Additionally, the outer leads can take the form of any shape other than a "curved" trapezoid. Obviously, the central lead 520e can have a cross section different than circular.

Figure 6:
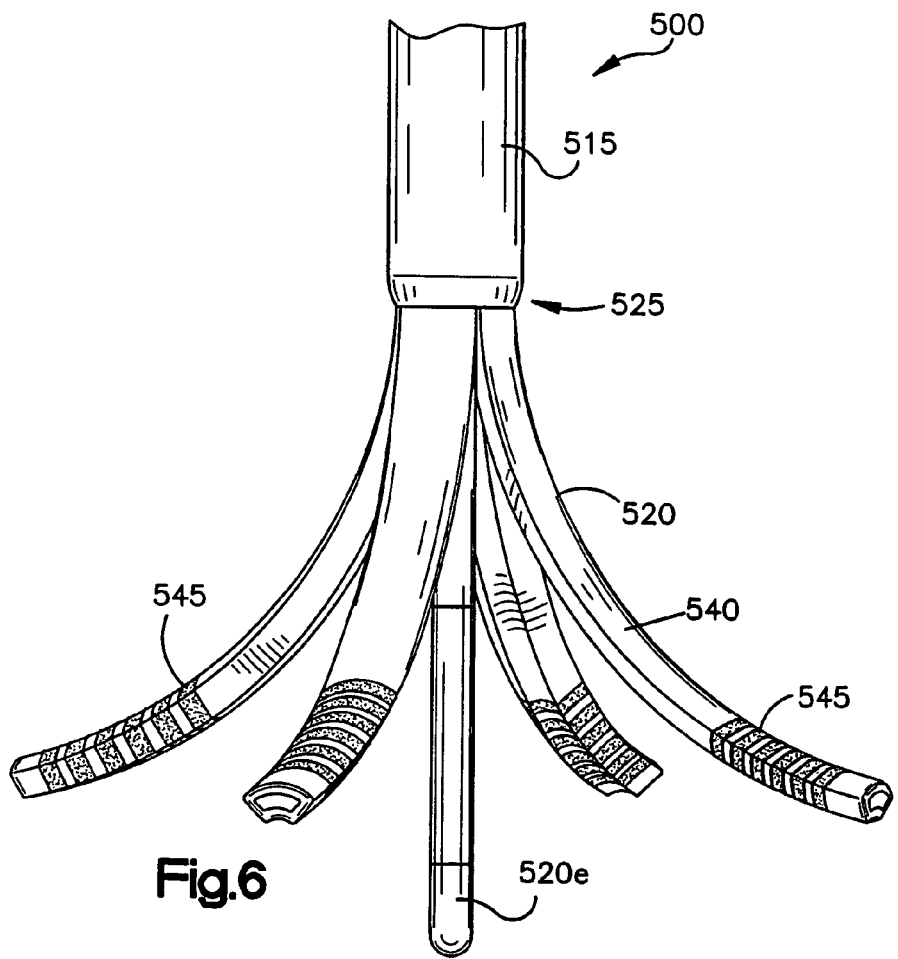
FIG. 6 illustrates a perspective view of the neurostimulation device 500 in the extended position.

FIG. 6 illustrates a perspective view of the neurostimulation device 500 in the extended position. In one embodiment, the leads 520 can be deployed in an array emanating generally from a target site within the treatment region of the tissue. For example, the array can be a three-dimensional array to reach a volume of tissue. To permit the leads to extend into a three-dimensional array, the leads 520 can be configured to be pre-bent into an arcuate shape and have a memory to retain such arcuate shape. For example, each lead has a spring memory causing them to assume an arcuate configuration and deflect radially outwardly as the leads are advanced distally relative to the cannula 515.

Each lead 520 can include a support form or substrate 540 having a plurality of electrodes 545. It will be appreciated that each individual electrode 545 can be selectively powerable. This control provides a desired, focused (i.e. directed) electrical field around each lead 520. Electrodes 545 may be positioned on the inside surface of the lead 520 towards the longitudinal axis of the device 500, or the outside surface of the lead 520 away from the longitudinal axis of the device 500, or combinations thereof. The shape of the field will vary with the power applied, the number and arrangement of electrodes, and particular shapes and sizes chosen for the electrodes. In another embodiment, the central lead 520e can include a drug infusion channel to provide medication to the target site.

Figure 7:
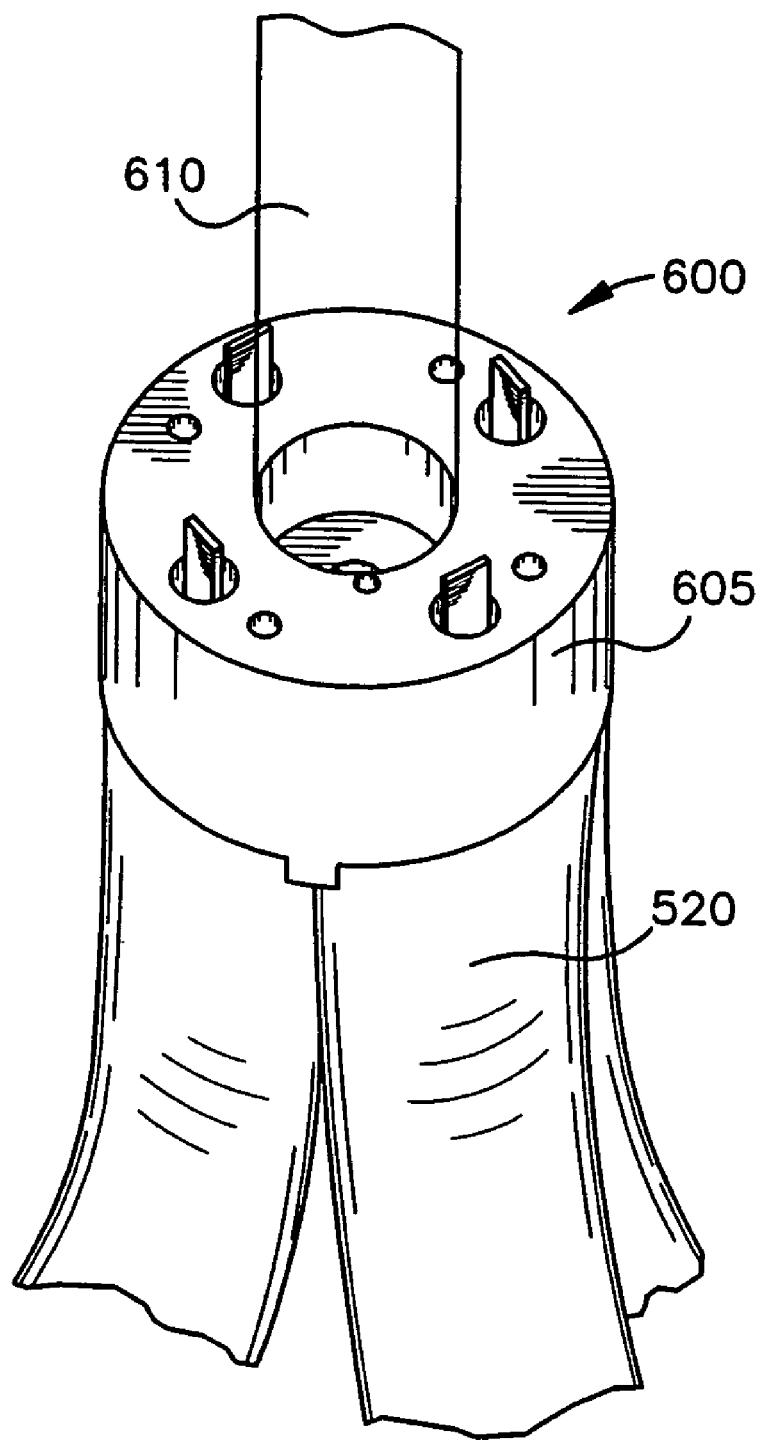
FIG. 7 illustrates one embodiment of an actuation mechanism 600 coupled to the leads 520 to permit the extension and retraction of the leads 520.

In one embodiment, the leads 520 can be movable between the retracted and extended positions by an actuation mechanism. Illustrated in FIG. 7 is one embodiment of an actuation mechanism 600 coupled to the leads 520 to permit the extension and retraction of the leads 520. The actuation mechanism 600 includes a cylindrical block 605 secured to a shaft 610. The leads 520 are connected at their proximal ends to the cylindrical block 605 such that the leads 520 move as the shaft 610 is advanced distally or retracted proximally relative to the cannula 515. The electrodes on the central lead 520e may be electrically coupled to the electrodes 545 on the outer leads 520a-d (in which case it acts as an additional electrode of the same polarity as the electrodes on the outer leads 520a-d) or may be electrically isolated from the electrodes. When the core is electrically isolated, it can remain neutral during a treatment protocol, or alternatively it may be energized in the opposite polarity and thus act as a return electrode in a bipolar treatment protocol. Alternatively, the central lead 520e may move independently of the outer leads 520a-d.

In operation, the device 500 will be first introduced into the target site where the leads 520 are in the retracted position. Once the device has been implanted, the leads 520 can be moved to the extended position by advancing the actuation mechanism 600 in an axial direction away from the distal end of the cannula 515 such that the leads 520 are deployed in the desired three-dimensional array. In one embodiment, the leads 520 can diverge radially outwardly from the cannula 515 (located at the target site) into the target site in a uniform pattern, i.e. with the spacing between adjacent electrodes diverging in a substantially uniform and/or symmetric pattern. In the exemplary embodiments, pairs of adjacent leads will be spaced-apart from each other in similar or identical, repeated patterns and will usually be symmetrically positioned about an axis of the cannula 515. It will be appreciated that a wide variety of particular patterns can be provided to uniformly cover the region to be treated.

Illustrated in FIGS. 8A-8D are multiple views of another embodiment of a neuromodulation device 800 configured to deploy multiple leads out of a single opening in a three-dimensional volume of tissue. The neuromodulation device 800 includes a cannula 810 and a guide 815 that is positioned at a distal end 817 of the cannula 810. The guide 815 is secured to a shaft 820 such that axial movement of the shaft 820 results in axial movement of the guide 815 away from the distal end 817 of the cannula 810 as shown by arrow A in FIG. 8A. The device 800 can also include a plurality of leads 825 contained in the cannula 810 that surround the shaft 820.

Figure 8D:
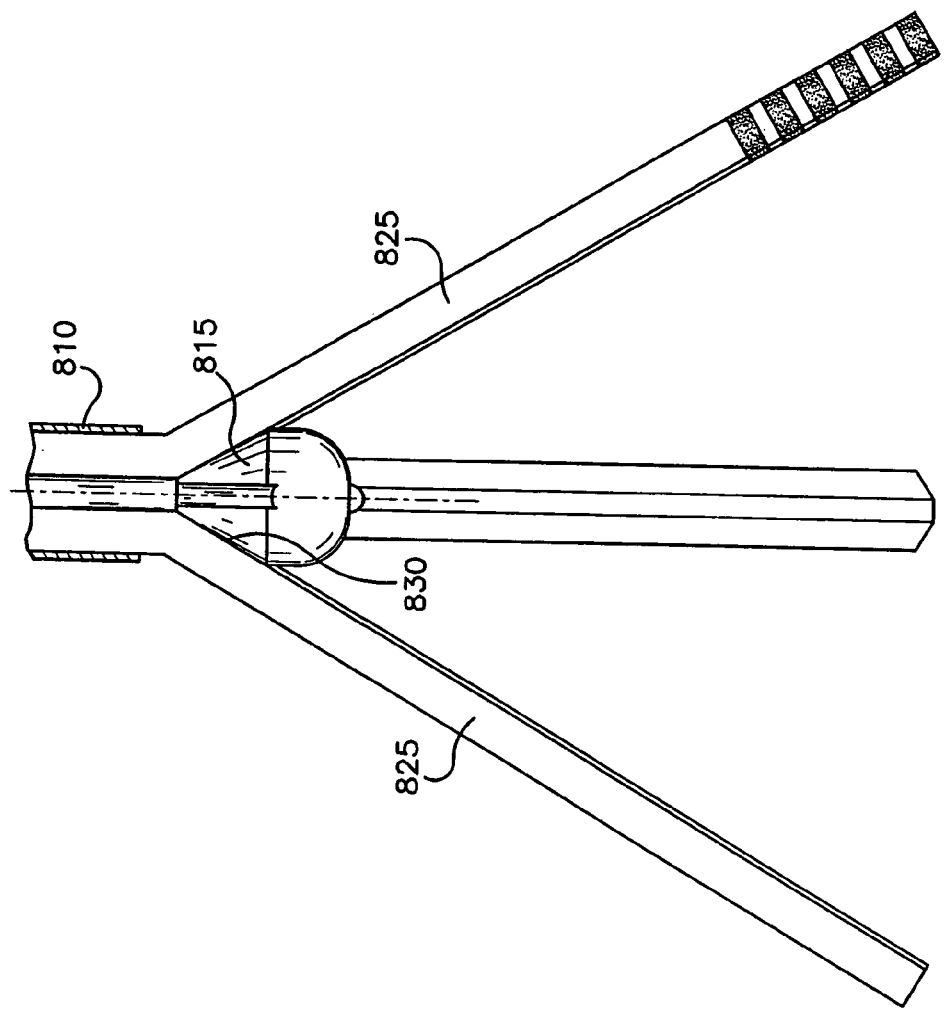
Figure 8C:
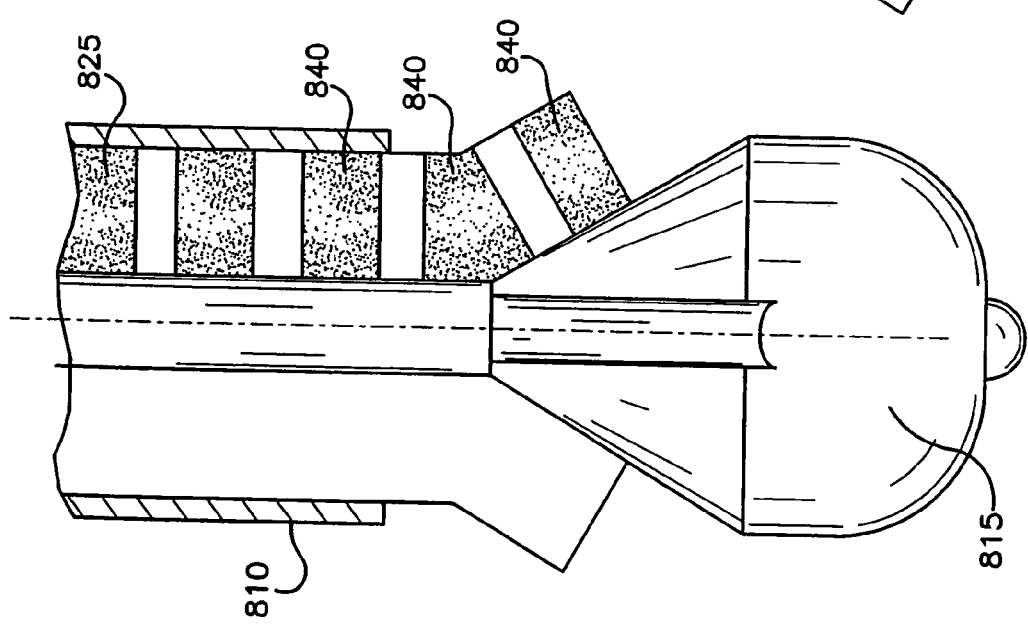

As shown in FIG. 8B, the guide 815 can include a plurality of recessed tracks 830 positioned on an outer surface that are configured to direct the leads 825 in an outwardly direction away from the cannula 810 when the leads 825 are advanced out of the cannula 810 as shown in FIGS. 8C and 8D.

Each lead 825 can include one or more electrodes 840 provided on its distal end such that each can be selectively powerable as discussed above by individually connecting each electrode 840 to a signal generator (not shown) through cables (not shown). Electrodes 840 may be positioned on the inside surface of the lead 825 towards the longitudinal axis of the device 800, on the outside surface of the lead 825 away from the longitudinal axis of the device 800, or combinations thereof. Optionally, the guide 815 may include an electrode 840 positioned at its tip. Electrodes 840 may be selectively powered as an anode, cathode or neither.

In one embodiment, the leads 825 may be coupled to an actuator mechanism similar to the one described above and illustrated in FIG. 6. Alternatively, the leads may be coupled to a different mechanism to advance the leads, individually or all together, into the target site. In another embodiment, the leads may be inserted manually one at a time.

In operation, as shown in FIGS. 8C and 8D, the guide 815 is first advanced away from the cannula 810. Once the guide 815 is fully advanced, the leads 825 may be advanced out of the cannula 810 towards the guide 815 either individually, in pairs, or all together. Once a lead 825 reaches its respective track 830 in the guide 815, the lead 825 is directed along the angle of the track 830 that protrudes out away from the cannula 810. Accordingly, the leads 825 may be directed outwardly away from the cannula 810 and occupy a three-dimensional volume of tissue.

Figure 10:
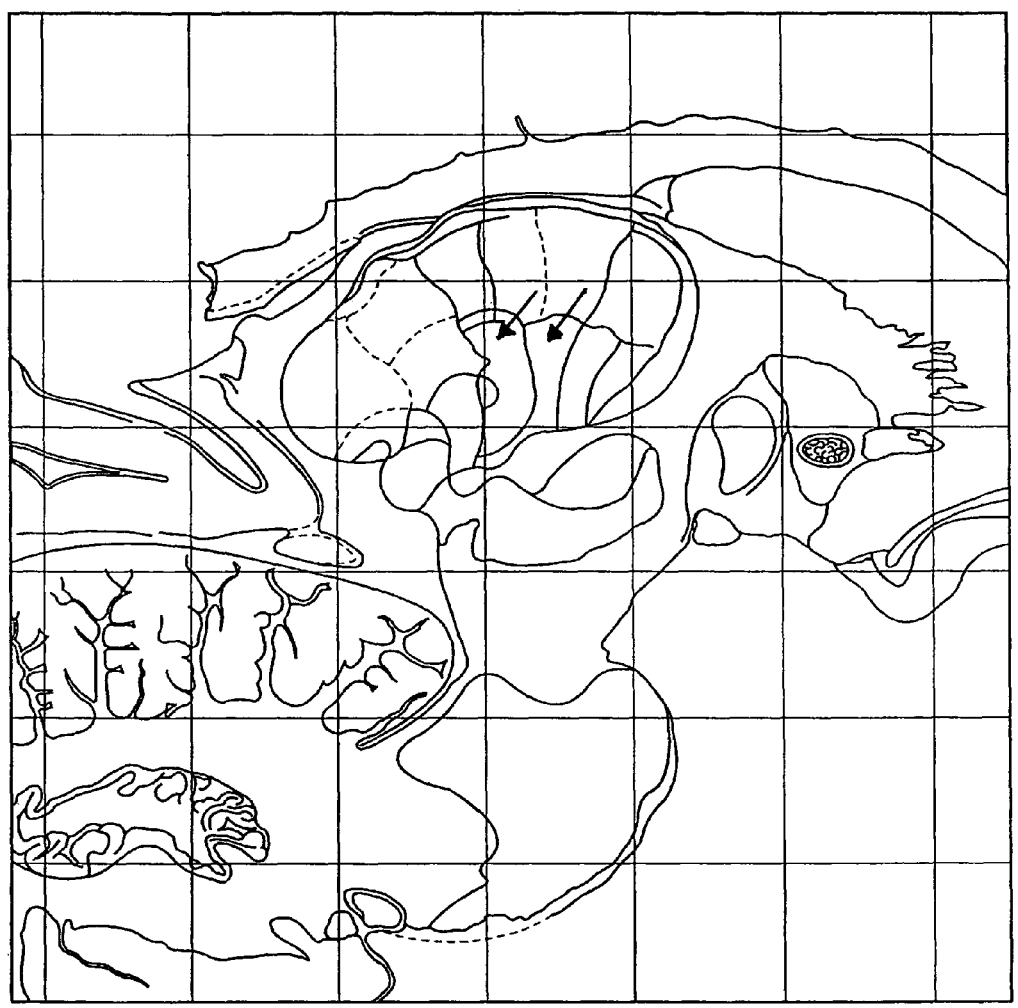
FIG. 10 illustrates a cross section of the human brain sectioned through the dentate nucleus.

The present invention may be used to modulate any number of sites in the brain or to modulate particular neuronal bodies which may include neurons, axons, and other constituents of neuronal tissue as is known in the art. As shown in FIGS. 9 and 10, particular sites within the brain include, for example, the subthalamic nucleus (STN), the peduncular pontine nucleus (PPN), the caudate or putamen, the internal and external pallidum, the cingulum, the anterior limb of the internal capsule, the anterior nucleus (AN), the centremedian (CM), the dorsal medial nucleus and other nuclei of the thalamus, the lateral nucleus, the hippocampus and other structures in the temporal lobe, the hypothalamus and other structures of the diencephalon, the pons, the medulla, the cortex, the cerebellum, the lateral geniculate body, and the medial geniculate body. As shown in FIG. 10, the arrows indicate particular relevant treatment sites. The desired configuration of the electrodes would depend upon the structure of the portion of the brain to be modulated or infused and the angle of introduction of the deep brain cannula.

The present invention may also be implemented alone or in combination with a drug delivery system to provide chemical modulation utilizing a drug, pharmaceutical, or therapeutic agent. In this embodiment, a pump and catheter is provided either alone or in combination with the signal generator and the electrode. The pump may be implanted below the skin of a patient and has a port into which a hypodermic needle can be inserted through the skin to inject a quantity of a liquid agent, such as a drug, pharmaceutical, or therapeutic agent. The liquid agent is delivered from pump through a catheter port into a catheter. The catheter is positioned to deliver the liquid agent to a predetermined region of the brain.

Optionally, the present invention may incorporate a closed-loop feedback system to provide automatic adjustment of the electrical and/or chemical modulation therapy. The system may incorporate a sensor to provide feedback to provide enhanced results. Sensor can be used with a closed loop feedback system in order to automatically determine the level of electrical and/or chemical stimulation necessary to provide the desired treatment. Sensor may be implanted into a portion of a patient's body suitable for detecting symptoms of the disorder being treated. Sensor is adapted to sense an attribute of the symptom to be controlled or an important related symptom. Sensors suitable for this purpose may include, for example, those disclosed in U.S. Pat. No. 5,711,316, which is incorporated herein by reference in its entirety. In cases where the attribute of the symptom is the electrical activity of the brain, stimulating electrodes may be intermittently used to record electrical activity. Alternatively, one or more electrodes implanted within the brain may serve as a sensor or a recording electrode. When necessary, these sensing or recording electrodes may deliver stimulation therapy to the predetermined region of the brain. The output of an external feedback sensor may communicate with the implanted pulse generator through a telemetry down-link.

Furthermore, although the preferred embodiments described above indicate the use of a cannula to enter the brain of a patient, one skilled in the art would appreciate that the present invention may be practiced without the use of a cannula or with a modified cannula.

Also, although the above described preferred embodiments detail that the lead that is capable of being bent, capable of being pre-bent such that the lead has a memory bend, or capable of being pre-formed into a desired shape that has memory such as a shape memory alloy (SMA), the lead still should be stiff enough to be advanced through the cannula, yet flexible enough to be bent as the lead is being advanced through the cannula. Also, the lead may be advanced with or without a stylet. The stylet may provide certain advantages in guiding the lead in the desired direction to reach the predetermined region of the brain.

The operator or patient preferably may also selectively adjust the energy, amplitude or pulse parameters delivered to each electrode. The selective control over each electrode may be achieved by employing a programmer which is coupled via a conductor to a telemetry antenna. The programmer is capable of sending signals via the telemetry antenna to control the electrical signal delivered to the electrodes and to control the actuator system. The system permits attending medical personnel to select the various pulse output options after implant using telemetry communications. While the preferred system employs fully implanted elements, systems employing partially implanted generators and radio-frequency coupling may also be used in the practice of the present invention. Advantageously, the present invention allows the locus of excitation to be selectively adjusted and/or steered to precisely target portions of the brain to achieve the desired treatment therapy. The steering may be accomplished in the manner described in U.S. Pat. No. 5,713,922 which is incorporated herein by reference in its entirety.

To advance the lead through the cannula, an actuator system that creates linear motion may be provided (not shown). Two common actuator systems to create linear motion include a linear motor and a rotary motor that is coupled to a sub-system to convert rotary motion to linear motion. If a linear motor is used, then the linear motor would be coupled to the lead to provide the pushing and pulling effect, i.e., the advancement or retraction of the lead. Since the lead requires linear motion (i.e., to advance/retract), rotary motor should be coupled to sub-system such as a lead screw, rack and pinion, or the like to translate rotational motion to linear motion. Both the rotary motor and linear motor may be positioned at the proximal end of cannula or outside the cannula just below the scalp.

The lead may be provided within the cannula as part or the device or the lead may be installed during the surgical technique. If the lead is provided within the cannula as part of the device, the actuator system (not shown) should be provided at the proximal end of the cannula to control the advancement and retraction of the lead or the actuator system may be positioned outside the cannula just below the scalp. The lead should be flexible enough to be guided along an angled or bent path, yet rigid enough to be advanced or retracted through the guide. Optionally, the lead may be made of a silicon material or metal having a predetermined bend or memory along its body to ensure the lead projects from the aperture at the desired angle.

A component or element may be provided for introducing the cannula to the target site within the treatment region to be treated. For example, a conventional sheath and sharpened obturator (stylet) assembly can be used to initially access the target site. The assembly can be positioned under ultrasonic or other conventional imaging, with the obturator/stylet then being removed to leave an access lumen through the sheath. The leads can then be introduced through the sheath lumen, typically while constrained in the cannula. In some instances, the cannula may be insulated from the deployed electrodes but have an exterior surface configured to provide a common or ground electrode for bipolar operation.

Furthermore, it is understood that one ordinarily skilled in the art can appreciate the ability to select and power individual electrodes independently from other electrodes in order to stimulate the desired target region and to obtain desired directional properties. Specifically, this ability to control the energizing of electrodes enables a physician to focus (i.e. direct) an electrical field around the chosen powered electrode thus pinpointing the stimulation area. For example, if the lead has a circular cross-section and two half ring electrodes wrap around the lead on the same annular ring portion of the lead, but do not touch each other (i.e., there is a gap between them); the present invention provides means for selectively turning on one of the half ring electrodes while turning off the other half ring electrode and vice versa. Accordingly, the half ring electrode that is turned on stimulates an area adjacent thereto while the other half ring electrode that is turned off does not stimulate the area adjacent thereto. Additionally, the shape of the electric field will vary corresponding to the power applied, the number and arrangement of electrodes, and particular shapes and sizes chosen for the electrodes. Also, each electrode may be selectively powered as an anode, cathode or neither.

The present invention also contemplates a navigation system that provides the surgeon/operator with the exact position/orientation of the cannula within the brain after the cannula and lead is deployed in the brain. For example, if the cannula has a circular cross-section (i.e. 360 degrees), it would be helpful for a surgeon/operator to know at which compass direction (i.e., degree) the cannula is positioned relative to a reference point in the brain. Thus, if the surgeon/operator knew exactly where the cannula was positioned, they could make knowledgeable decisions about which electrodes to deploy or turn on. Preferably, the mechanism would be some type of marker that is integral with the cannula, lead, or burr hole device that would show up under a CT or MRI scan. Accordingly, you could print the scan and feed it into a computer having navigational software and a three-dimensional atlas of the patient's brain to model approximately where all of the electrodes are positioned. The software then may be capable of providing you with instructions on where best to deploy the lead or which exact electrodes to turn off or on.

Additionally, the present invention contemplates that the device described above is not only capable of being adjusted intra-operatively, but also is capable of being adjusted post-operatively. Specifically, the lead positioning may be physically adjusted (advanced, retracted, or moved to a different location) in the brain post-operatively through the use of telemetry, RF signals, or other systems known in the art. The cannula need only be inserted once while the lead may be re-positioned in the brain tissue multiple times to reach the desired area of the brain. Further, the electrodes on the lead may be adjusted post-operatively by turning them on/off, adjusting the voltage, adjusting the frequency, and adjusting other electrical signal parameters through the use of telemetry, RF signals, or other systems known in the art. Also, if chemical stimulation is also provided, the ports may be opened or closed or the amount of drug being delivered may be adjusted post-operatively through the use of telemetry, RF signals, or other systems known in the art.

Those skilled in the art will appreciate that electrical properties of the electrodes and the resulting electrical field may be varied by selectively powering individual or groups of electrodes formed from or controlled by micro-electrical mechanical systems (MEMS). Moreover, MEMS actuators may drive electrodes, drug delivery catheters, sensing probes and the like from the cannula to desired locations in an area of interest.

The present invention contemplates methods and implantable systems that ameliorate, prevent or treat a disease condition in the brain or other neuronal tissue. Specifically, this involves combining a method of supplying a coerce of a genetic expression vehicle with a stimulation device. More specifically, this involves the repopulation of the diseased site with undifferentiated cells or DNA expression vehicles and augmentation of the repopulated cells or DNA expression vehicle with electrical stimulation to cause the newly formed tissue to express desired neurochemicals or neuronal activity.

The repopulation of the neuronal tissue can be carried out using a cellular or a molecular approach. Cellular approaches involve the injection, either directly or via infusion, for example, of undifferentiated cells, preferably cultured autologous cells, into the desired region of the neuronal tissue. Molecular approaches involve the injection, either directly or via infusion, for example, of nucleic acid, whether in the form of naked, plasmid DNA, optionally incorporated into liposomes or other such delivery vehicle or a genetically engineered vector into the area to be treated or enhanced. The genetically engineered vector can include a viral expression vector such as a retrovirus, adenovirus, or an adeno-associated viral vector, for example.

A desired area of neuronal treatment can be determined by one of skill in the art. Near the area of neuronal treatment means within about 1 centimeter (cm) of the edge of the treatment or electrical stimulation area. These regions are shown for example in FIGS. 9 and 10.

The cells or genetic material can be delivered simultaneously with the electrical stimulation device, or they can be delivered separately. In one embodiment, the electrical stimulation device is the carrier of the cells or genetic material. The electrical stimulation device typically includes an implantable stimulator and electrodes.

The nucleic acid molecules, preferably recombinant nucleic acid molecules, can be prepared synthetically or, preferably, from isolated nucleic acid molecules, as is know in the art. A nucleic acid is "isolated" when purified away from other cellular constituents, such as, for example, other cellular nucleic acids or proteins, by standard technique known to those of ordinary skill in the art. The coding region of the nucleic acid molecule can encode a full length gene product or a fragment thereof or a novel mutated or fusion sequence. The coding sequence can be a sequence endogenous to the target cell, or exogenous to the target cell. The promoter, with which the coding sequence is operably associated, may or may not be one that normally is associated with the coding sequence. Importantly, the present invention allows for genetic information to be turned on or off based upon electrical stimulation provided by the electrical stimulation device. Accordingly, amplitude, intensity, frequency, duration etc. of the electrical signal may be used to selectively control expression of genetic materials or constructs delivered to the target area. U.S. Pat. No. 6,151,525 which is hereby incorporated by reference thereto to the extent it supports the present application describes the use of electrical current to modify undifferentiated contractile cells to form tissue capable of forming new contractile tissue.

The invention has been described with reference to the preferred embodiments. Modifications and alterations will occur to others upon reading and understanding the preceding Detailed Description. It is intended that the invention be construed as including all such modifications and alterations insofar as they come within the scope of the appended claims or the equivalents thereof.

What is claimed is:

1. A device for modulating a volume of neural tissue, comprising:
   a cannula having a proximal end, a distal end, and a lumen extending to at least the distal end;
   a plurality of leads having at least one electrode disposed thereon, wherein the plurality of leads are configured to reciprocate between a retracted position, in which the plurality of leads are radially constrained within the lumen, and an extended position, in which the plurality of leads deploy radially outwardly into the neural tissue;
   a guide provided at the distal end of the cannula, said guide having a bulbous-shaped distal portion configured to deflect the plurality of leads radially outwardly into the neural tissue when the plurality of leads are moved to the extended position, and to block the plurality of leads from extending from the lumen of the cannula when the plurality of leads are in the retracted position; and
   a shaft connected to the guide, the shaft being at least partially positioned in the lumen of the cannula, wherein axial movement of the shaft causes axial movement of the guide.

2. The device of claim 1, wherein at least one of the leads is shaped so that it assumes an outwardly everted configuration as it extends distally into the neural tissue from the distal end of the cannula.

3. The device of claim 1, wherein the plurality of leads includes two leads, each lead having a semi-circular cross-sectional configuration.

4. The device of claim 1, wherein the plurality of leads includes four outer leads that project outwardly from the cannula when in the extended position.

5. The device of claim 1, further comprising an actuator mechanism, wherein the plurality of leads are coupled to the actuator mechanism to reciprocate between the retracted position and the extended position.

6. The device of claim 5, wherein the actuation mechanism includes a cylindrical block coupled to the shaft.

7. The device of claim 6, wherein each of the plurality of leads is coupled to the cylindrical block.

8. The device of claim 1, wherein the guide and the distal end of the cannula form an opening therebetween to permit the plurality of leads to exit the cannula.

9. The device of claim 1, wherein the guide includes grooves to assist in the deflection of the plurality of leads outwardly into the neural tissue.

10. The device of claim 1, wherein the guide includes an electrode disposed thereon.

11. The device of claim 1, wherein the guide is secured to a distal end of a shaft.

12. The device of claim 11, wherein the plurality of leads are received in the space between the shaft and a wall of the cannula.

13. The device of claim 1, wherein the guide includes recessed tracks on an outer surface of the guide for receiving the leads therein.

14. The device of claim 1, wherein the guide is independently extendable from the cannula.

15. The device of claim 1, wherein the plurality of leads comprises four outer leads, each having a curved trapezoidal cross-sectional configuration.

* * * * *